US006147056A

United States Patent [19]
Gilchrest et al.

[11] Patent Number: 6,147,056
[45] Date of Patent: Nov. 14, 2000

[54] USE OF LOCALLY APPLIED DNA FRAGMENTS

[75] Inventors: Barbara A. Gilchrest, Boston; Mina Yaar, Sharon; Mark Eller, Boston, all of Mass.

[73] Assignee: Trustees of Boston University, Boston, Mass.

[21] Appl. No.: 09/048,927

[22] Filed: Mar. 26, 1998

Related U.S. Application Data

[63] Continuation-in-part of application No. PCT/US96/08386, Jun. 3, 1996, and a continuation-in-part of application No. 08/952,697, Dec. 6, 1997, which is a continuation-in-part of application No. 08/467,012, Jun. 6, 1995, Pat. No. 5,955,059.

[51] Int. Cl.$^7$ .......................... A61K 48/00; A61K 9/127; A61K 31/70
[52] U.S. Cl. ................................. 514/44; 514/43; 514/45; 514/46; 514/47; 424/450
[58] Field of Search ................................. 514/44, 43, 45, 514/46, 47; 424/59, 450

[56] References Cited

U.S. PATENT DOCUMENTS

| | | | |
|---|---|---|---|
| 3,937,809 | 2/1976 | Jacobi | 424/60 |
| 4,419,343 | 12/1983 | Pauly | 424/59 |
| 4,508,703 | 4/1985 | Redziniak et al. | 424/38 |
| 4,621,023 | 11/1986 | Redziniak et al. | 428/402.2 |
| 5,077,211 | 12/1991 | Yarosh | 435/193 |
| 5,455,029 | 10/1995 | Hartman et al. | 424/94.4 |
| 5,470,577 | 11/1995 | Gilchrest et al. | 424/450 |
| 5,599,672 | 2/1997 | Liang et al. | 435/6 |
| 5,643,556 | 7/1997 | Gilchrest et al. | 424/59 |
| 5,879,713 | 3/1999 | Roth et al. | 424/489 |
| 5,955,059 | 9/1999 | Gilchrest et al. | 424/59 |

FOREIGN PATENT DOCUMENTS

| | | |
|---|---|---|
| 035384 | 9/1981 | European Pat. Off. . |
| WO 93/09788 | 5/1993 | WIPO . |
| WO 93/22431 | 11/1993 | WIPO . |
| WO 95/01773 | 1/1995 | WIPO . |
| WO 95/07362 | 3/1995 | WIPO . |
| WO 95/09175 | 4/1995 | WIPO . |
| WO 96/40989 | 12/1996 | WIPO . |
| WO 97/44450 | 12/1996 | WIPO . |

OTHER PUBLICATIONS

Principles of Biochemistry, 6th edition. White et al., eds. pp. 182–183, 1978.

Fritsch, M. et al., "Induction of nuclear accumulation of the tumor–suppressor protein p53 by DNA–damaging agents," *Oncogene* 8:307–318 (1993).

Mitsudomi, T. et al., "p53 gene mutations in non–small–cell lung cancer cell lines and their correlation with the presence of ras mutations and clinical features," *Oncogene* 7:171–180 (1992).

Nelson, W.G. and Kastan, M.B., "DNA Strand Breaks: the DNA Template Alterations That Triger p53–Dependent DNA Damage Response Pathways," *Mol. and Cell. Biol.* 14(3):1815–1823 (1994).

Wei, Q. et al., "DNA repair and aging in basal cell carcinoma: A molecular epidemiology study," *Proc. Natl. Acad. Sci. USA* 90:1614–1618 (1993).

Yaar, M. et al., "The trk Family of Receptors Mediates Nerve Growth Factor and Neurotrophin–3 Effects in Melanocytes," *J. Clin. Invest* 94:1550–1562 (1994).

Mitchell, D.L. and Karentz, D., "The Induction and Repair of DNA Photodamage in the Environment," In *Environment UV Photobiology*, A.R. Young et al., eds. (NY: Plenum Press), pp. 345–377 (1993).

Pedeux, R., et al., "Thymidine Dinucleotides Induce S Phase Cell Cycle Arrest in Addition to Increased Melanogenesis in Human Melanocytes," The Society for Investigative Dermatology, Inc., (pp. 472–477) (1998).

Niggli, H.J. et al., "Sunlight–Induced Pyrimidine Dimers In Human Skin Fibroblasts In Comparison With Dimerization After Artificial UV–Irradiation", *Photochemistry and Photobiology*, 48(3):353–356 (1988).

Jayaraman, L. and Prives, C., "Activation of p53 Sequence–Specific DNA Binding by Short Single Strands of DNA Requires the p53 C–Terminus", *Cell*, 81:1021–1029 (1995).

Kern SE., et al., "Oncogenic Forms of p53 Inhibit p53–regulated Gene Expression," *Science*, 256(5058):827–30 (1992).

Walworth, N.C. and Bernards, R., "rad–Dependent Response of the chkl–Encoded Protein Kinase at the DNA Damage Checkpoint," *Science*, 271:353–356 (1996).

El–Deiry, W.S., et al., "WAF1, a Potential Mediator of p53 Tumor Suppression," *Cell*, 75:817–825 (1993).

Lu, X. and D.P. Lane, "Differential Induction of Transcriptionally Active p53 Following UV or Ionizing Radiation: Defects in Chromosome Instability Syndromes?" *Cell*, 75:765–778 (1993).

Kastan, M.B. et al., "A Mammalian Cell Cycle Checkpoint Pathway Utilizing p53 and GADD45 Is Defective in Ataxia–Telangiectasia," *Cell*, 71:587–597 (1992).

Hupp, T.R. et al., "Small Peptides Activate the Latent Sequence–Specific DNA Binding Function of p53," *Cell*, 83:237–245 (1995).

Sanchez, Y. et al., "Regulation of RAD53 by the ATM–Like Kinases MEC1 and TEL1 in Yeast Cell Cycle Checkpoint Pathways," *Science*, 271:357–360 (1996).

*Primary Examiner*—Deborah J. Clark
*Attorney, Agent, or Firm*—Hamilton, Brook, Smith & Reynolds, P.C.

[57] ABSTRACT

Methods of treatment or prevention of hyperproliferative diseases or pre-cancerous conditions affecting epithelial cells, such as psoriasis, vitiligo, atopic dermatitis, or hyperproliferative or UV-responsive dermatoses, hyperproliferative or allergically mediated diseases of other epithelia and methods for reducing photoaging or for prophylaxis against or reduction in the likelihood of the development of skin cancer, are disclosed.

5 Claims, 11 Drawing Sheets

SEQUENCE LISTING

<160> NUMBER OF SEQ ID NOS: 4

<210> SEQ ID NO 1
<211> LENGTH: 9
<212> TYPE: DNA
<213> ORGANISM: Artificial Sequence
<220> FEATURE:
<223> OTHER INFORMATION: DNA Fragment

```
<400> SEQUENCE: 1 gagtatgag                                                                                9

<210> SEQ ID NO 2
<211> LENGTH: 9
<212> TYPE: DNA
<213> ORGANISM: Artificial Sequence
<220> FEATURE:
<223> OTHER INFORMATION: DNA Fragment

<400> SEQUENCE: 2 taggaggat                                                                                9

<210> SEQ ID NO 3
<211> LENGTH: 7
<212> TYPE: DNA
<213> ORGANISM: Artificial Sequence
<220> FEATURE:
<223> OTHER INFORMATION: DNA Fragment

<400> SEQUENCE: 3 agtatga                                                                                  7

<210> SEQ ID NO 4
<211> LENGTH: 5
<212> TYPE: DNA
<213> ORGANISM: Artificial Sequence
<220> FEATURE:
<223> OTHER INFORMATION: DNA Fragment

<400> SEQUENCE: 4 gtatg                                                                                    5
```

USE OF LOCALLY APPLIED DNA FRAGMENTS

RELATED APPLICATION(S)

This application is a Continuation-in-Part of U.S. National Phase of PCT/US96/08386 filed Jun. 3, 1996, and assigned U.S. application Ser. No. 08/952,697, filed Dec. 6, 1997, which is a Continuation-in-Part of application Ser. No. 08/467,012 filed Jun. 6, 1995, now U.S. Pat. No. 5,955,059 the entire teachings of which are incorporated herein by reference.

BACKGROUND OF THE INVENTION

Human skin consists of two layers, the dermis and the epidermis. The epidermis, which is the uppermost of the two skin layers, encompasses many different cell types, including melanocytes and keratinocytes. Melanocytes are specialized cells in the basal layer of the epidermis which synthesize melanin; the melanin is then packaged into melanosomes and then transported into keratinocytes. Exposure of skin to the sun results in vitamin D synthesis, sunburn (erythema), and tanning, the skin's major form of endogenous protection against subsequent skin damage from ultraviolet (UV) irradiation. Various morphologic and enzymatic changes occur at the cellular level in epidermal melanocytes in response to UV irradiation. Melanin, which is increased in "tanned" skin, serves as a filter with absorbance within the UV range and provides photoprotection for the individual.

The peak action spectrum for erythema is in the UV-B range, 290–305 nm. UV-B rays are absorbed by proteins and nucleic acids of the epidermis, causing the production of thymine dimers, which are known to be formed by UV irradiation of nuclear DNA and to be excised from the DNA strand by the action of highly specific enzymes, including endonucleases. If not removed, these dimers can stall DNA replication forks generating regions of single-stranded DNA. Failure to remove thymine dimers and other forms of DNA damage in the genome may lead to somatic mutations resulting in carcinogenesis.

In bacteria it is known that single-stranded DNA released as fragments during the course of DNA repair or exposed at stalled replication forks can interact with nuclear proteins which then regulate the expression of specific genes in the DNA as part of the organism's SOS response to UV damage. The tanning response of skin might reasonably be considered part of the analogous SOS response in mammalian skin. The precise stimulus for UV-induced tanning, however, remains unknown.

UV irradiation is successfully used in phototherapy and photochemotherapy for certain dermatological conditions. For example, psoriasis is a common dermatologic disease affecting 1 to 2 percent of the population. Psoriasis can be treated with UV-B irradiation, either alone or in conjunction with agents such as coal tar or anthralin, or with UV-A irradiation in combination with psoralens (PUVA therapy). Other diseases which respond to UV irradiation treatment include atopic dermatitis and vitiligo. Despite the benefits of phototherapy and photochemotherapy, these treatments carry the same risks as chronic exposure to sun, including wrinkling, "photoaging," and skin cancer.

SUMMARY OF THE INVENTION

The present invention pertains to repair for any type of DNA damage, in whole or in part, by induction of DNA repair mechanisms such as nucleotide excision repair. The DNA damage can be caused by ultraviolet irradiation, or by exposure to DNA-damage inducing chemicals or carcinogens, such as benzo(a)pyrene (BP).

The current invention further pertains to methods of treating or preventing hyperproliferative diseases or precancerous conditions affecting epithelial cells, such as psoriasis or other skin diseases, including contact dermatitis and other hyperproliferative, pre-cancerous or UV-responsive dermatoses, in a mammal. The invention further comprises methods of prophylaxis against skin cancer or reduction in the likelihood of development of skin cancer, as well as reduction of severity of photoaging resulting from sun exposure, in a mammal, including humans. The methods comprise contacting cells (or introducing into cells) of a mammal with single-stranded DNA fragments, (e.g., oligonucleotides or polynucleotides) deoxynucleotides, dinucleotides, dinucleotide dimers or a mixture thereof, such that the DNA fragments, deoxynucleotides, dinucleotides, or dinucleotide dimers are available to the cells. Alternatively, cells are contacted with an agent that increases the activity of p53 protein and therefore stimulates nucleotide excision repair. The fragments, deoxynucleotides or dinucleotides, or agent that increase p53 activity resulting in an increase in nucleotide excision repair, can be introduced topically, orally, by aerosol, or by any other appropriate means, such as by instillation. The DNA fragments, or deoxynucleotides or dinucleotides can be ultraviolet-irradiated.

The invention also includes compositions useful in the above methods, comprising DNA fragments, deoxynucleotides, dinucleotides or dinucleotide dimers, or an agent that increases p53 activity and thus increases nucleotide excision repair, in an appropriate delivery vehicle, such as liposomes.

DETAILED DESCRIPTION OF THE INVENTION

Figure 1:
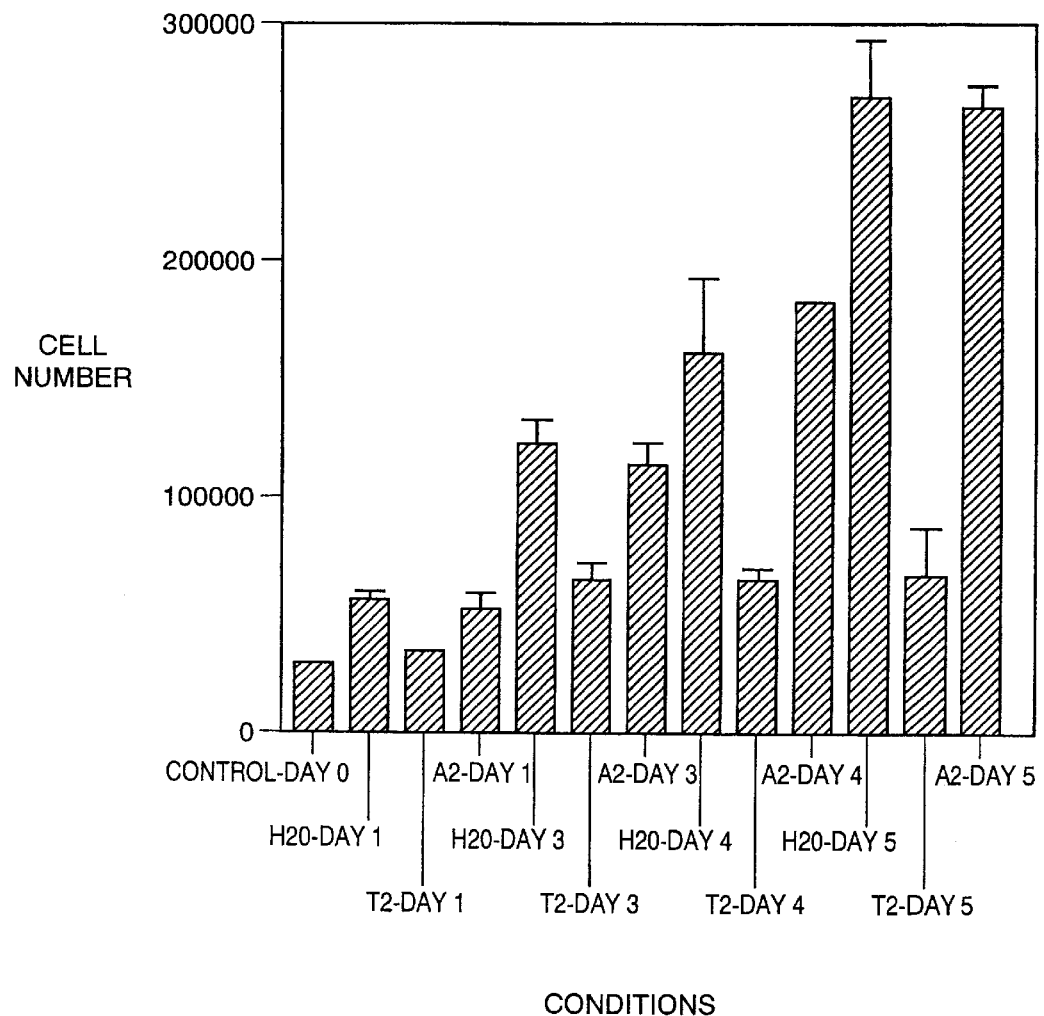
FIG. 1 is a graphic representation of the cell growth rate of human squamous carcinoma cells dosed with water (diluent), 100 $\mu$M pTpT ($T_2$) or 100 $\mu$M pdApdA ($A_2$). Day 0 is before dosage; days 1, 3, 4 and 5 are days after dosage.

The present invention is based on applicants discovery that treatment of cells with DNA fragments can elicit a protective response to subsequent exposure to UV-irradiation or chemicals. It is likely that pTpT, and other small nucleic acids, mimic the products of DNA damage or processed DNA-damage intermediates. These compounds previously have been shown to evoke a melanogenic (tanning) response in skin (U.S. Pat. No. 5,643,556, the teachings of which are incorporated herein in their entirety), thus recapitulating the melanogenic protective response to UV irradiation, and in the present invention is shown to result in induction of the p53 pathway, including up-regulation of p53 inducible genes involved in DNA repair, such as p21, proliferating cell nuclear antigen (PCNA) and xerodoma pigmentosum group A protein (XPA). The DNA fragments of the present invention mimic the DNA damage signal, resulting in induction of the nucleotide excision repair pathway and transient cellular growth arrest that permits more extensive DNA repair before cell division, in the absence of genotoxic stress. Such "mimicry" is useful in chemoprotection from carcinogenesis. Specifically, the invention pertains to use of DNA fragments, deoxynucleotides, dinucleotides, or dinucleotide dimers, as defined in the following description, or an agent that increases activity of p53 protein, for the prevention or treatment of certain hyperproliferative diseases or precancerous conditions affecting cells such as epithelial cells, keratinocytes or fibroblasts, including skin diseases such as psoriasis and hyperproliferative, pre-cancerous or UV-induced dermatoses such as contact dermatitis in mammals, and particularly in humans. The invention further pertains to use of DNA fragments, deoxynucleotides, dinucleotides, or dinucleotide diners, or agents that increase activity of p53 protein, for reduction of photoaging (a process due in part to cumulative DNA damage) or prophylaxis against or reduction in the likelihood of the development of skin cancer, in a mammal. The invention further provides compositions comprising said DNA fragments, deoxynucleotides, dinucleotides, or dinucleotide dimers, or agents that increase activity of p53 protein.

In one embodiment of the invention, DNA fragments of approximately 3–200 bases in length, deoxynucleotides (single bases), dinucleotides, or dinucleotide dimers, are administered to the mammal in an appropriate vehicle. As used herein, "DNA fragments" refers to single-stranded DNA fragments, double-stranded DNA fragments, or a mixture of both single- and double-stranded DNA fragments. "Deoxynucleotides" refers to either a single type of deoxynucleotide or a mixture of different deoxynucleotides. "Dinucleotides" can comprise a single type of nucleotide or different types of nucleotides, and can comprise a mixture of different types of dinucleotides. In a preferred embodiment, the nucleotides of the dinucleotides are deoxynucleotides. Representative dinucleotides include d(pT)₂, d(pC)₂, d(pA)₂, d(pCpT), d(pTpC), d(CpT), d(TpC) and d(TpT), where T is thymine, C is cytosine, d is deoxy, and p is phosphate (see Niggli, *Photochem. Photobiol.* 38(3):353–356 (1988)). A combination of at least two or more of DNA fragments, deoxynucleotides, dinucleotides, and/or dinucleotide dimers can also be used. The DNA fragments, deoxynucleotides, or dinucleotides can be ultraviolet-irradiated. Such ultraviolet irradiation results in photodimerization between two adjacent upyrimidine residues (i.e., thymine (T) and cytosine (C)) present in the DNA fragments or dinucleotides.

As shown by the present invention, thymidine dinucleotide decreases the cell growth rate of several human cell types including squamous cell carcinoma, cervical carcinoma, melanoma, neonatal keratinocytes and normal neonatal fibroblasts (Examples 1–5, respectively). pTpT also reduces epidermal turnover rate in a guinea pig model (Example 6). Furthermore, pTpT treatment of cells results in the nuclear localization of p53 (Example 7) and the induction of p53-regulated genes (Example 8) such as genes involved in DNA repair (Examples 1 and 7). Pretreatment of cells with pTpT enhances their ability to repair DNA damage by UV irradiation and by the chemical carcinogen benzo(a) pyrene (Examples 8 and 9), at least in part through activation of p53 and up-regulation of genes transcriptionally activated by p53, such as the p21/Waf/Cip 1 gene.

DNA fragments are also effective UV mimetics. For example, a nine-nucleotide oligomer, GAGTATGAG (SEQ ID No: 1) was able to stimulate melanogenesis in human melanocytes and induce the expression of p21/Waf/Cip 1 in a squamous cell carcinoma cell line. Furthermore, a scrambled version of the 9-mer, TAGGAGGAT (SEQ ID No: 2), and truncated versions of the original 9-mer, AGTATGA (SEQ ID No: 3), and GTATG (SEQ ID No: 4), were also able to stimulate melanogenesis in human melanocytes (Example 11). Thus, the UV-mimetic activity of pTpT is duplicated quite dramatically by oligonucleotides (e.g., in the 2–200 nucleotide range, typically in the 5 to 20 nucleotide range and most typically in the 5–10 nucleotide range). The oligonucleotides of the present invention are therefore useful in methods of preventing cancer and photoaging by enhancing DNA repair and by enhancing pigmentation by increasing melanin production. Melanin is known to absorb photons in the UV range and therefore its presence reduces the risk of cancer and photoaging.

Thymidine dinucleotide, pTpT, mimics some effects of UV light including inducing melanogenesis and stimulating keratinocyte production of TNFA (Example 4). TNFA is also induced by pTpT in a mouse contact hypersensitivity model (Example 10). The dinucleotide pdApdA fails to induce these responses.

UVB radiation is a potent inhibitor of the inductive phase of contact hypersensitivity (CH), and TNFa is a mediator of this suppressive effect. Thymidine dinucleotides (pTpT), the substrate for UW-induced thymine dimer formation, simulates several UVB effects including increased tyrosinase expression and melanin content in cultured melanocytes and skin tanning in guinea pigs. Adenine dinucleotides (pApA), less commonly dimerised by UF, are less effective. As shown in Example 9, these DNA fragments also mimic the suppressive effect of UVB on contact hypersensitivity in a mouse model. As demonstrated by the present invention, intracutaneous injection with pTpT can inhibit the induction of contact hypersensitivity and can activate the TNFα gene in vivo. These findings expand the spectrum of UVB effects mimicked by pTpT and demonstrate that DNA photoproducts and/or their repair mediate the biologic consequences of UVB radiation.

The DNA fragments, deoxynucleotides, dinucleotides, or dinucleotide dimers can be obtained from any appropriate source, or can be synthetic DNA fragments, deoxynucleotides, dinucleotides, or dinucleotide dimers. For example, salmon sperm DNA can be dissolved in water, and then the mixture can be autoclaved to fragment the DNA.

An "agent that increases activity of p53 protein," as used herein, is an agent (e.g., a drug, molecule, nucleic acid fragment, or nucleotide) that increases the activity of p53 protein and therefore results in increase in DNA repair mechanisms, such as nucleotide excision repair, by the induction of proteins involved in DNA repair, such as PCNA and XPA. The activity of p53 protein can be increased by directly stimulating transcription or translation of p53 DNA or RNA; by increasing expression or production of p53 protein; by increasing the stability of p53 protein; by increasing the resistance of p53 mRNA or protein to degradation; by causing p53 to accumulate in the nucleus of a cell; by increasing the amount of p53 present; or by otherwise enhancing the activity of p53. The p53 protein itself is also an agent that increases the activity of p53 protein. A combination of more than one agent that increases the activity of p53 can be used. Alternatively or in addition, the agent that increases the activity of p53 can be used in combination with DNA fragments, deoxynucleotides, or dinucleotides, as described above.

The DNA fragments, deoxynucleotides, dinucleotides or dinucleotide dimers, or agents that increase the activity of p53 protein, can be applied alone or in combination with other compounds, such as perfumes or colorants. They can be applied in a vehicle, such as water, saline, or in another appropriate delivery vehicle. The delivery vehicle can be any appropriate vehicle which delivers the DNA fragments, deoxynucleotides, dinucleotides, or dinucleotide dimers, or agent that increases the activity of p53 protein. In one embodiment, propylene glycol is used as a delivery vehicle. In a preferred embodiment, a mixture of propylene glycol:ethanol:isopropyl myristate (1:2.7:1) containing 3% benzylsulfonic acid and 5% oleyl alcohol is used. In another embodiment, a liposome preparation is used. The liposome preparation can be comprised of any liposomes which penetrate the stratum corneum and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used.

The delivery vehicle can contain perfumes, colorants, stabilizers, sunscreens, or other ingredients.

The DNA fragments, deoxynucleotides, dinucleotides, or dinucleotide dimers, or agent that increases p53 activity, are applied to (introduced into or contacted with) the cells of interest in an appropriate manner. The "cells of interest", as used herein, are those cells which may become affected or are affected by the hyperproliferative disease or precancerous condition, or cells which are affected by DNA-damaging conditions such as UV irradiation or exposure to DNA damaging chemicals such as benzo(a)pyrene. Specifically encompassed by the present invention are epithelial cells, including melanocytes and keratinocytes, as well as oral, respiratory, bladder and cervical epithelial cells. As demonstrated herein the methods and compositions of the present invention inhibit growth of epithelial cells from numerous sources.

In one embodiment, the DNA fragments, deoxynucleotides, dinucleotides, or dinucleotide dimers, or agent that increases p53 activity, are applied topically to the skin surface. In other embodiments, the DNA fragments, deoxynucleotides, dinucleotides, or dinucleotide dimers, or agent that increases p53 activity, are delivered to other epithelial that are recognized to have a lesser barrier to entry of such substances than does the skin, such as orally to the oral or intestinal epithelium; by aerosol to the respiratory epithelium; by instillation to the bladder epithelium; or by other means to other cells or tissues in the body. The DNA fragments, deoxynucleotides, dinucleotides, or dinucleotide dimers, or agent that increases p53 activity, are applied at an appropriate time, in an effective amount. The "appropriate time" will vary, depending on the type and molecular weight of the DNA fragments, deoxynucleotides, dinucleotides, or dinucleotide dimers, or agent, employed; the condition to be treated or prevented; the results sought; and the individual patient. An "effective amount", as used herein, is a quantity or concentration sufficient to achieve the desired result. The effective amount will depend on the type and molecular weight of the DNA fragments, deoxynucleotides, dinucleotides, or dinucleotide dimers, or agent, employed; the condition to be treated or prevented; the results sought; and the individual patient. For example, for the treatment or prevention of psoriasis, or for hyperproliferative, precancerous, or UV-induced dermatoses, the effective amount is the amount necessary to relieve the symptoms of the disease, to reduce the area of skin affected by the disease, or to prevent the formation of affected areas. The concentration will generally be approximately 2–300 $\mu$m, and will depend on the type and molecular weight of the DNA fragments, deoxynucleotides, dinucleotides, or dinucleotide dimers, or agent, employed; the condition to be treated or prevented; the results sought; and the individual patient. In a preferred embodiment, the concentration is 50–200 $\mu$m; in a more preferred embodiment, the concentration is 75–150 $\mu$m.

In a first embodiment of the current invention, DNA fragments, such as single-stranded DNA fragments, deoxynucleotides, dinucleotides, or dinucleotide dimers, or an agent that increases p53 activity, are applied, either without a vehicle or in an appropriate delivery vehicle, to the cells of interest in the mammal in order to treat or prevent a hyperproliferative disease affecting epithelial cells. The DNA fragments, deoxynucleotides, dinucleotides, or dinucleotide dimers, or agent that increases p53 activity, can be applied solely to affected areas, or can be applied prophylactically to regions commonly affected by the hyperproliferative disease.

In a preferred embodiment of the invention, the DNA fragments, deoxynucleotides, dinucleotides, or dinucleotide dimers, or agent that increases p53 activity, are applied, either without a vehicle or in an appropriate delivery vehicle, to the epidermis for the treatment or prevention of psoriasis. The DNA fragments, deoxynucleotides, dinucleotides, or dinucleotide dimers, or agent that increases p53 activity, can be applied solely to affected areas, or can be applied prophylactically to regions of epidermis commonly affected.

In another preferred embodiment of the invention, the DNA fragments, deoxynucleotides, dinucleotides, or dinucleotide dimers, or agent that increases p53 activity, are applied, either without a vehicle or in an appropriate delivery vehicle, to the epidermis for the treatment or prevention of atopic dermatitis, contact dermatitis or allergically mediated inflammation of other epithelia such as allergic rhinitis or allergic conjunctivitis (hayfever) in a mammal. The DNA fragments, deoxynucleotides, dinucleotides, or dinucleotide dimers, or agent that increases p53 activity, can be applied solely to affected areas, or can be applied prophylactically to regions of epidermis commonly affected. In another preferred embodiment of the invention, the DNA fragments, deoxynucleotides, dinucleotides, or dinucleotide dimers, or agent that increases p53 activity, are applied, either alone or in an appropriate delivery vehicle, to the epidermis for the treatment or prevention of vitiligo. The DNA fragments, deoxynucleotides, dinucleotides, or dinucleotide dimers, or agent that increases p53 activity, can be applied solely to affected areas, or can be applied prophylactically to regions of epidermis commonly affected.

In another preferred embodiment, DNA fragments, deoxynucleotides, dinucleotides, or dinucleotide dimers, or agent that increases p53 activity, are applied, either alone or in an appropriate delivery vehicle, to the epidermis for the treatment or prevention of other hyperproliferative, precancerous or UV-responsiveness dermatoses.

In a second embodiment, DNA fragments, deoxynucleotides, dinucleotides, or dinucleotide dimers, or an agent that increases p53 activity, are applied, either alone or in an appropriate delivery vehicle, to the epidermis for reduction of photoaging, or prophylaxis against or reduction in the likelihood of development of skin cancer. The DNA fragments, deoxynucleotides, dinucleotides, or dinucleotide dimers, or agent that increases p53 activity, are applied at an appropriate time (i.e., sufficiently close in time to exposure of the skin to UV irradiation): the DNA fragments, deoxynucleotides, dinucleotides, or dinucleotide diners can be applied before, during or after exposure to UV irradiation. They can be applied daily or at regular or intermittent intervals. In a preferred embodiment, the DNA fragments, deoxynucleotides, dinucleotides, or dinucleotide dimers, or agent that increases p53 activity, can be applied on a daily basis to skin which may be exposed to sunlight during the course of the day.

In a further embodiment of the invention, the DNA fragments deoxynucleotides, dinucleotides, or dinucleotide dimers, or agent that increases p53 activity, are applied, either without a vehicle or in an appropriate delivery vehicle, to cells of an individual (e.g., epithelial cells) for the treatment or prevention of hyperproliferative, pre-cancerous conditions, or to repair or prevent DNA damage caused by DNA damaging chemicals, such as benzo(a)pyrene.

The invention is further illustrated by the following Examples.

EXAMPLE 1

Application to Human Squamous Carcinoma Cells

Human squamous carcinoma cells line SCC12F cells were maintained in primary keratinocyte medium (300 ml DME, 100 ml F-12 nutrient supplement, 50 ml 10× Adenine, 50 ml fetal bovine serum, 5 ml penicillin/streptomycin stock, and 0.5 ml of 10 µg/ml epidermal growth factor and hydrocortisone to final concentration of 1.4 µg/ml) and dosed with either water (diluent), 100 µM pTpT ($T_2$, Midland Certified Reagent Company, Midland, Tex.) or 100 µM pdApdA ($A_2$). Cells were harvested before dosing (day 0), and 1, 3, 4, and 5 days after dosage, and were counted by Coulter counter. After harvesting, the cells were processed for total RNA isolation and were analyzed by Northern blot. Addition of pTpT ($T_2$) to human squamous carcinoma cells resulted in marked decreases in cell growth rate, as shown in FIG. 1. Addition of a control deoxyadenine dinucleotide (pdApdA or $A_2$), a compound very similar to pTpT but not readily dimerized by UV irradiation and therefore not excised during the course of UV-induced DNA repair, has no effect (A).

Figure 2:
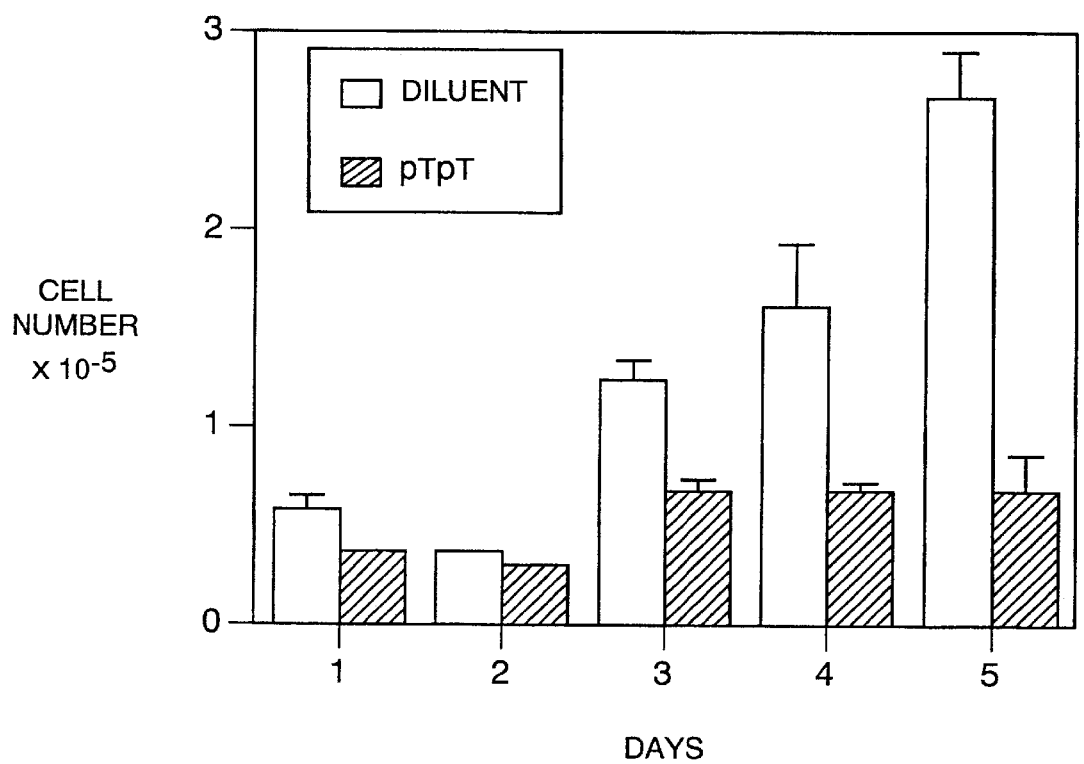
FIG. 2 is a graphic representation of the cell growth rate of normal human fibroblasts dosed with water (diluent) or 100 $\mu$M pTpT ($T_2$). Day 0 is before dosage; days 1, 3, 4 and 5 are days after dosage. Values represent averages ± standard deviations of duplicate cultures.

In a second experiment, SCC12F cells were cultured as described above. Two or three days after seeding, the preconfluent cultures were given fresh medium supplemented with either 100 µM $T_2$ or diluent as a control. Cells were collected by trypsinization daily and counted by Coulter counter. The cell yield in cultures treated with $T_2$ was reduced by 75% compared to that of paired control cultures after five days (FIG. 2). This corresponds to 2.3 population doublings in this time for control cells, compared with 1 doubling for $T_2$-treated cells. These results further demonstrate that application of the DNA fragments inhibits cell multiplication, including multiplication of cancerous cells.

In a third experiment, it was demonstrated that addition of thymidine dinucleotides ($T_2$) to human squamous carcinoma cells for 24–72 hours resulted in upregulation of at least three genes: growth arrest and DNA damage (GADD 45), senescence-derived inhibiter (Sdi I), and excision repair cross-complementing (ERCC-3) (data not shown). Paired cultures of SCC12F cells were maintained in a Dulbecco's modified Eagle's Medium (DMEM; GIBCO/BRL, Gaithersburg, Md.)-based keratinocyte growth medium supplemented with 10% fetal calf serum (Hyclone Labs, Logan, Utah) and epidermal growth factor as described (Hollander, M. C. et al., J. Biol. Chem. 268:328–336 (1992)). Pre-confluent cultures were given fresh medium supplemented with either 100 µM pTpT, or an equal volume of diluent. Cells were collected daily after additions and processed for total RNA isolation using the Tri-Reagent extraction method (Molecular Research Center, Cincinnati, Ohio) following the protocol of the manufacturer. Ten micrograms of RNA from each sample was gel electrophoresed, transferred to a nylon filter and probed as described previously (Nada, A. et al., Exp. Cell Res. 211:90–98 (1994)). The cDNA for GADD 45 was generated by PCR using primers based on the human GADD 45 gene sequence (Mitsudomi, T. et al., Oncogene 7:171–180 (1992)). The EDNA for ERCC 3 was purchased from the American Type Culture Collection (ATCC, Rockville, Md.). The SDI 1 cDNA was a gift of Dr. J. Smith and has been described previously (Walworth, N. C. and Bernards, R., Science 271:353–356 (1996)).

Compared to the diluent control, the mRNAs for GADD 45, ERCC 3 and SDI 1 were up-regulated in pTpT-treated cells as early as 24 hours, and remained elevated for several days. Addition of the control deoxyadenine dinucleotide ($A_2$) was less effective or ineffective in inducing these genes (data not shown). Comparable data have been obtained in preliminary experiments with S91 melanoma cells, and normal human fibroblasts (data not shown).

The time course of induction is similar to that observed after UV irradiation for the two genes for which this has been studied (GADD 45 and Sdi I) (Fornace, A. J. et al., Proc. Natl. Acad. Sci. USA 85:8800–8804 (1988); Hollander, M. C. et al., J. Biol. Chem. 268:24385–24393 (1993); Zhan, Q. et al., Mol. Cell Biol. 14:2361–2371 (1994); El-Deiry, W. S. et al., Cancer Res. 54:1169–1174 (1994); and El-Deiry, W. S. et al., Cell 75:817–825 (1993)) and also similar to the time course of induction of the tyrosinase gene by $T_2$ in melanocytes and melanoma cells (Maltzman, W. and L.Czyzyk, Mol. Cell Biol. 4:1689–1694

(1984); and Lu, X. and D. P. Lan, Cell 75:765–778 (1993)). Sdi I is known to be involved in cell cycle regulation and specifically in blocking cell division. GADD 45 and ERCC-3, a human DNA repair enzyme, are known to be involved in repair of UV-induced DNA damage. The response to pTpT is identical to that observed after UV irradiation of these cell lines, and is also similar to the response to various antimetabolites, such as methotrexate, that are clinically effective in the treatment of hyperproliferative skin disorders.

EXAMPLE 2

Application to Human Cervical Carcinoma Cells

Human cervical carcinoma cells (HeLa cells) were maintained in DME+10% calf serum and dosed with either water (diluent) or 100 $\mu$M pTpT (T2). Cells were collected 1, 4 and 6 days after dosage and counted by Coulter counter.

Figure 3:
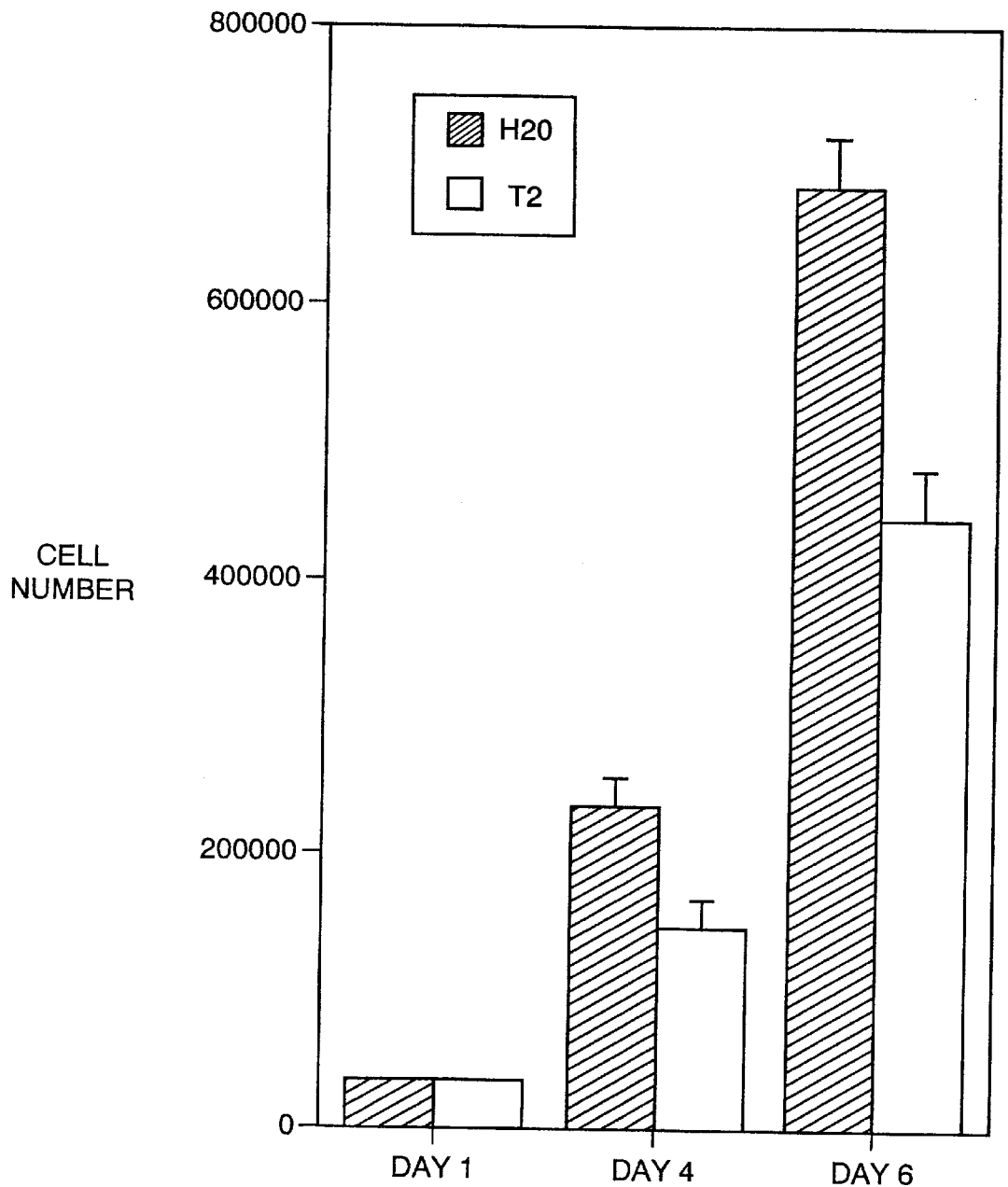
FIG. 3 is a graphic representation of the cell growth rate of human cervical carcinoma cells dosed with either water (diluent) or 100 $\mu$M pTpT ($T_2$). Day 0 is before dosage; days 1, 4 and 6 are days after dosage.

Addition of pTpT ($T_2$) to the human cervical carcinoma cells resulted in marked decreases in cell growth rate, as shown in FIG. 3.

EXAMPLE 3

Application to Human Melanoma Cells

Human melanoma cell lines CRL 1424, Malma, Sk Mel 2, and Sk Mel 28 were obtained from the American Type Culture Collection (ATCC). The cell lines were maintained in DME+2% calf serum, and dosed with either water (diluent) with DME, or 100 $\mu$M pTpT (T2) in DME. One week after dosage, cells were collected and counted by Coulter counter.

Figure 4:
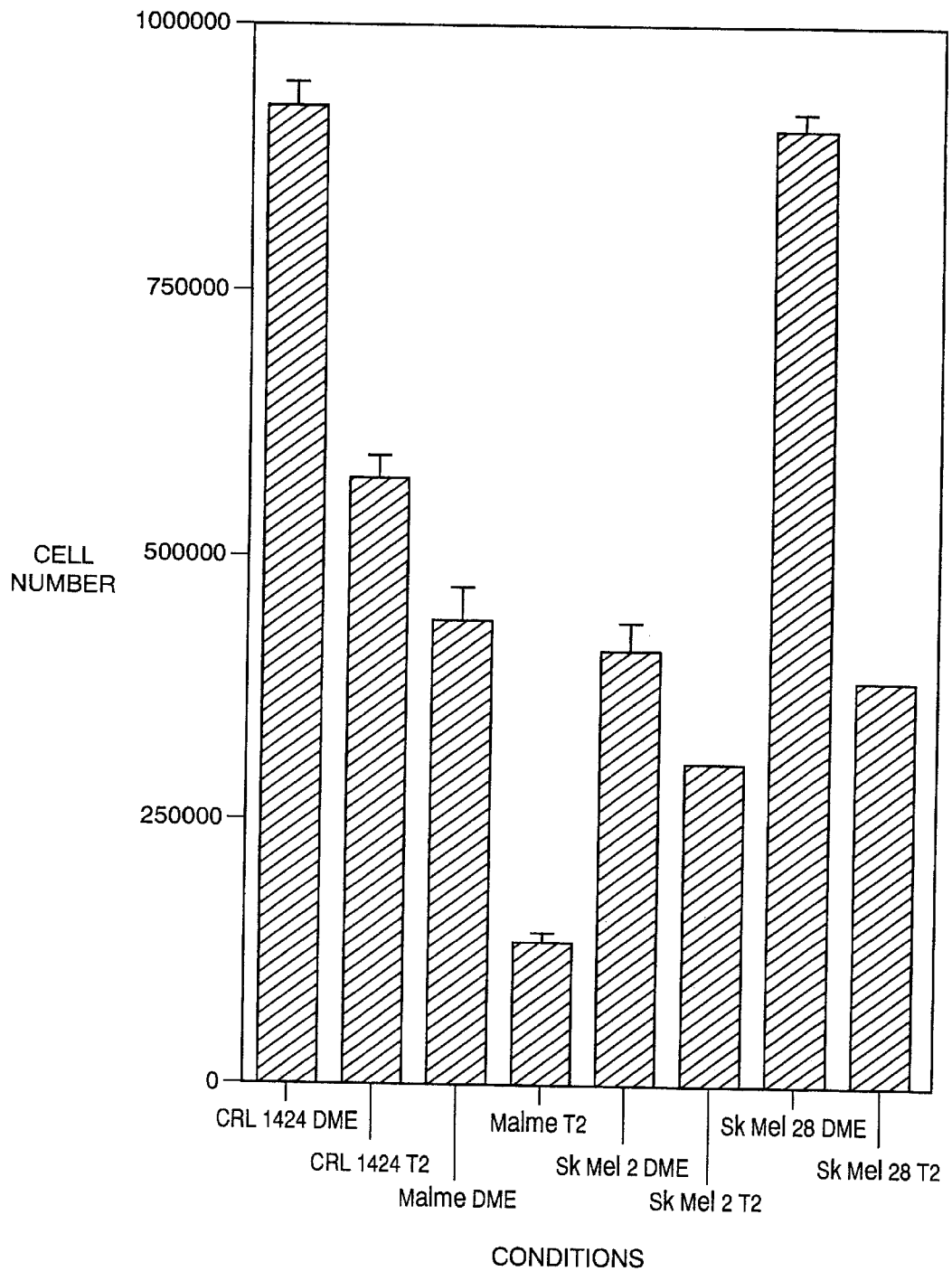
FIG. 4 is a graphic representation of the cell yield of human melanoma cell lines dosed with either diluent or 100 $\mu$M pTpT ($T_2$).

Addition of pTpT ($T_2$) to any of the four different human melanoma cell lines results in marked decreases in cell yields, as shown in FIG. 4.

EXAMPLE 4

Application to Human Keratinocytes

Figure 5:
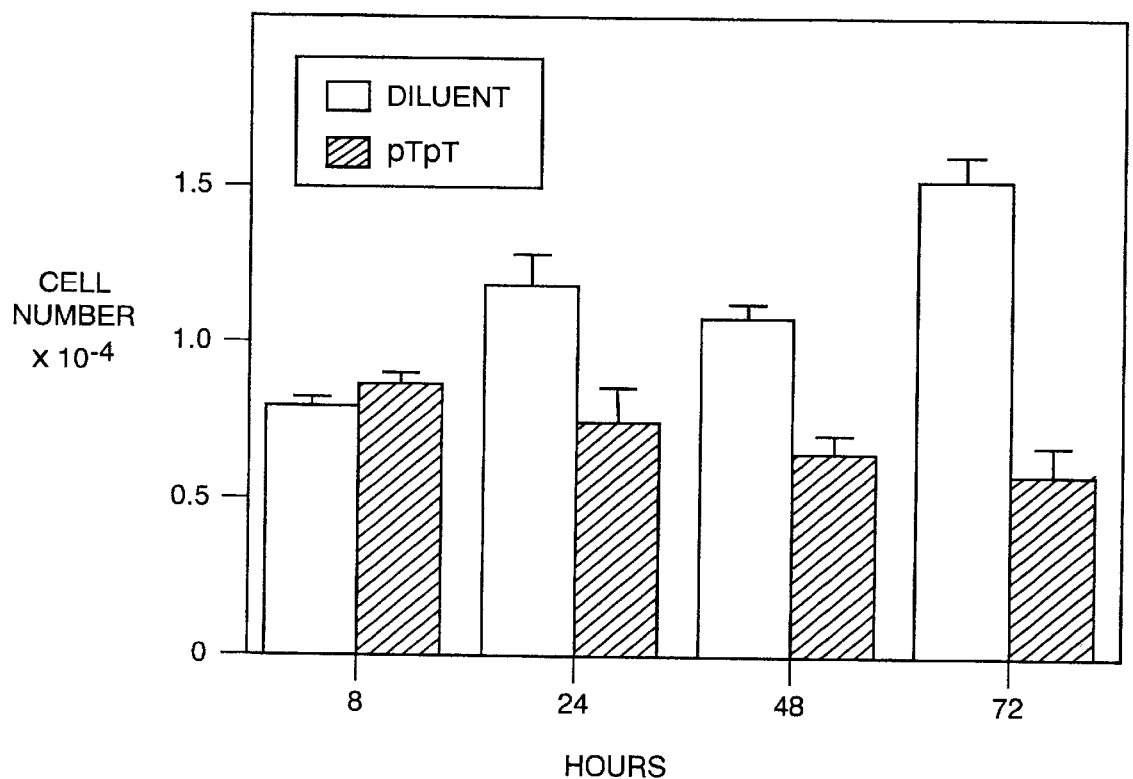
FIG. 5 is a graphic representation of the cell growth rate of normal human keratinocytes dosed with water (diluent) or 100 $\mu$M pTpT ($T_2$). Day 0 is before dosage; 8, 24, 48 and 72 are hours after dosage. Values represent averages±standard deviations of duplicate cultures.

Normal human neonatal keratinocyte cells were cultured as described above in Example 1 for SCC12F cells, and treated with either 100 $\mu$M $T_2$ or diluent as a control. Cells were harvested for cell counts. The cell yield in cultures treated with $T_2$ was reduced by 63% compared to that of paired control cultures after three days (FIG. 5). This corresponds to one population doubling in this time for control cells, while the number of $T_2$-treated cells remained the same. These results demonstrate that application of the DNA fragments inhibits cell multiplication.

Northern blot analysis of the normal human keratinocytes treated with pTpT for 24–72 hours that shows induction of the tumor necrosis factor (TNF) alpha gene (data not shown). This immunomodulatory cytokine, known to be induced by UV irradiation, may thus be induced by pTpT. Use of locally applied DNA fragments, deoxynucleotides, dinucleotides, or dinucleotide dimers may therefore be useful in immunodulation of cutaneous reactions and in treatment or prevention of diseases or conditions involving immune mediators.

EXAMPLE 5

Inhibition of Cell Growth of Normal Neonatal Fibroblasts by DNA Fragments

Figure 6:
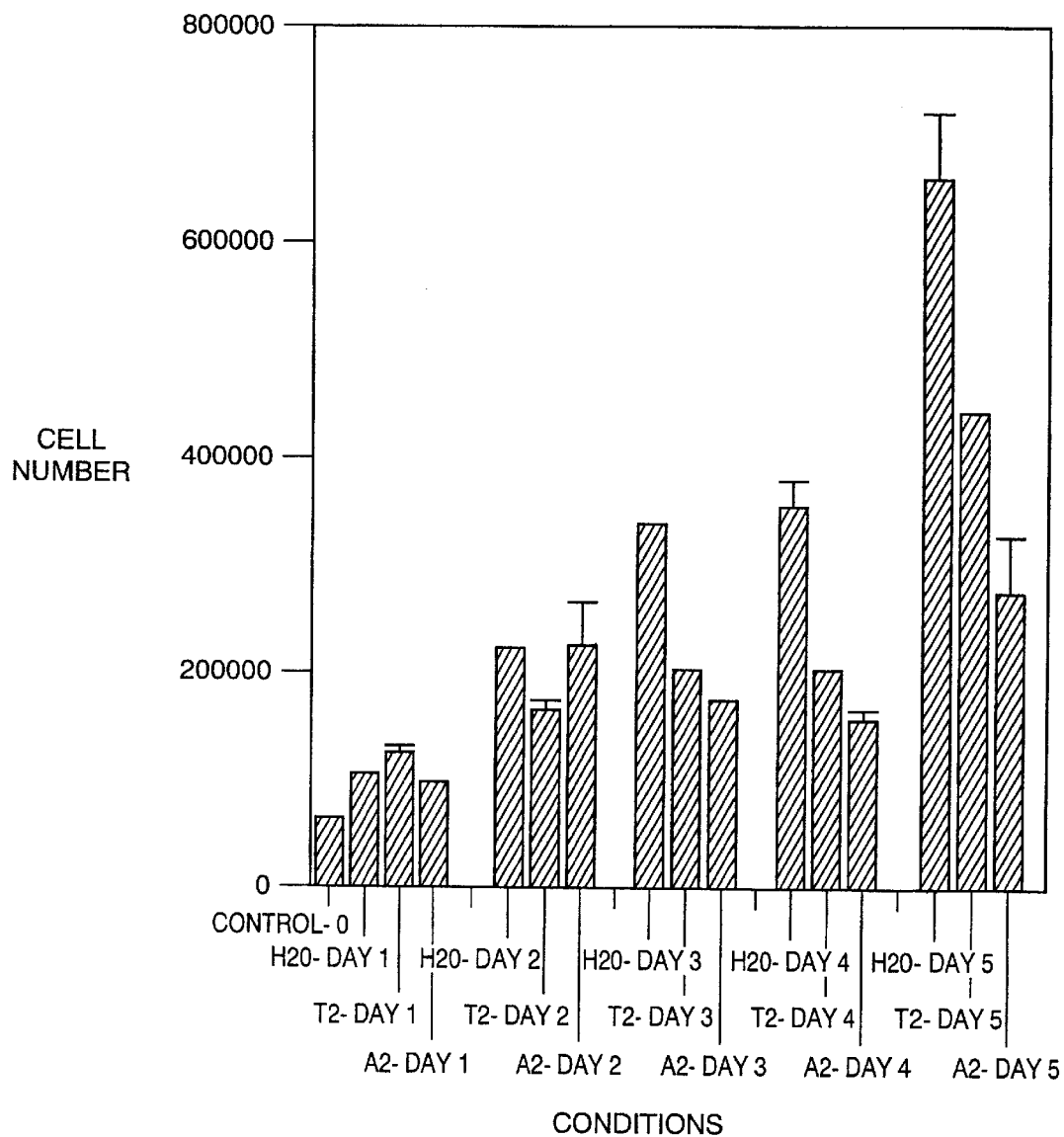
FIG. 6 is a graphic representation of the average cell number of human neonatal fibroblasts dosed with either water, $T_2$ or $A_2$.
Figure 7:
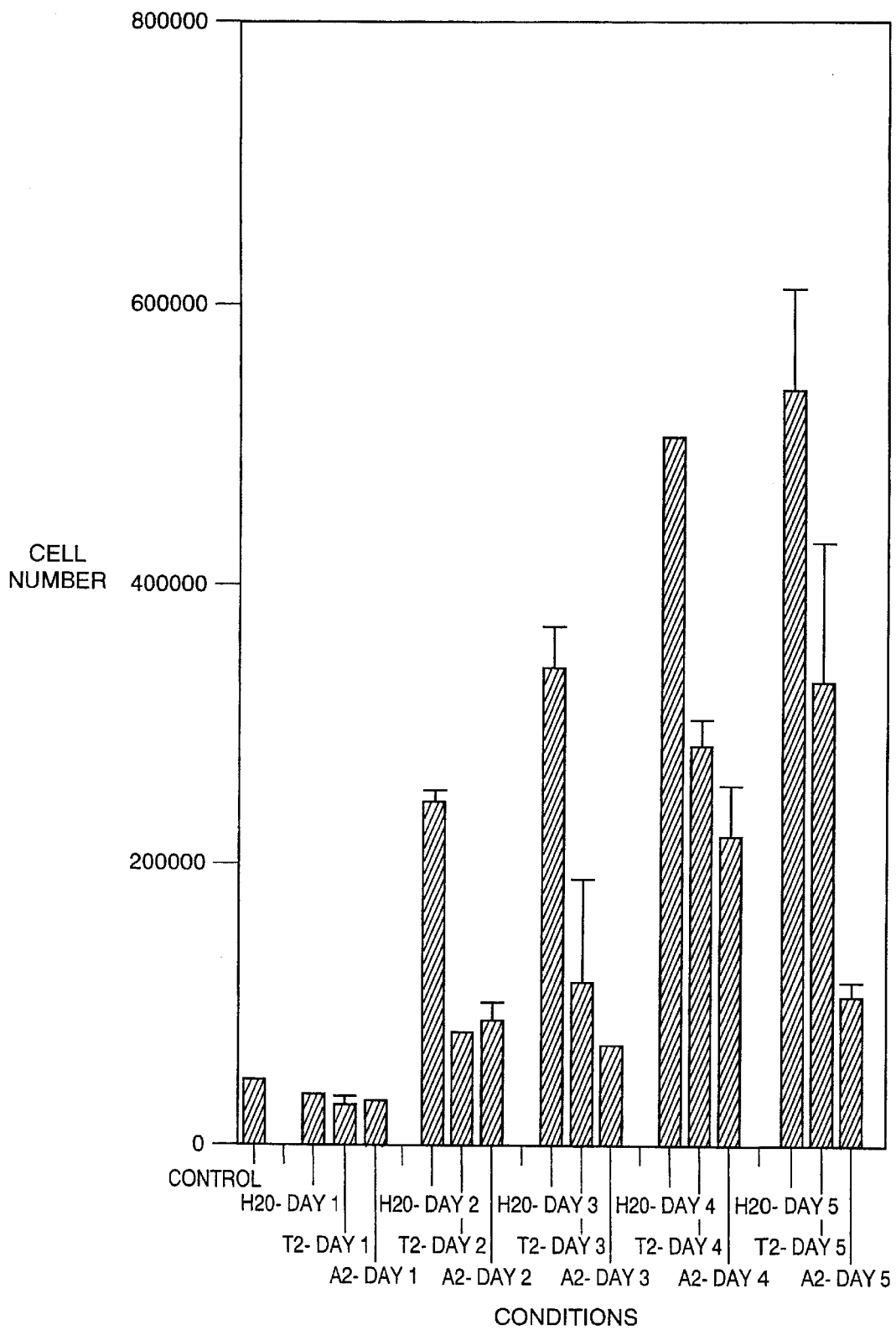
FIG. 7 is a graphic representation of the average cell number of human neonatal fibroblasts dosed with either water, $T_2$ or $A_2$.

Normal human neonatal fibroblasts were plated in Falcon P35 culture dishes at a density of $9 \times 10^4$ cells/dish. The culture medium was DME+10% calf serum, 2 ml per plate. One day after plating, cultures were supplemented with either 100 $\mu$l 2 mM $T_2$ in DME or 100 $\mu$l 2 mM $A_2$ in DME, or water (control). Two plates were collected and counted before the additions to give a starting, or "day 0," reading. Duplicate plates of each condition were harvested through five days after addition of the supplements and cell number determined. All cell counts were done by Coulter Counter. Results are shown in FIGS. 6 and 7. The results indicate that application of the DNA fragments inhibits cell multiplication.

Figure 8:
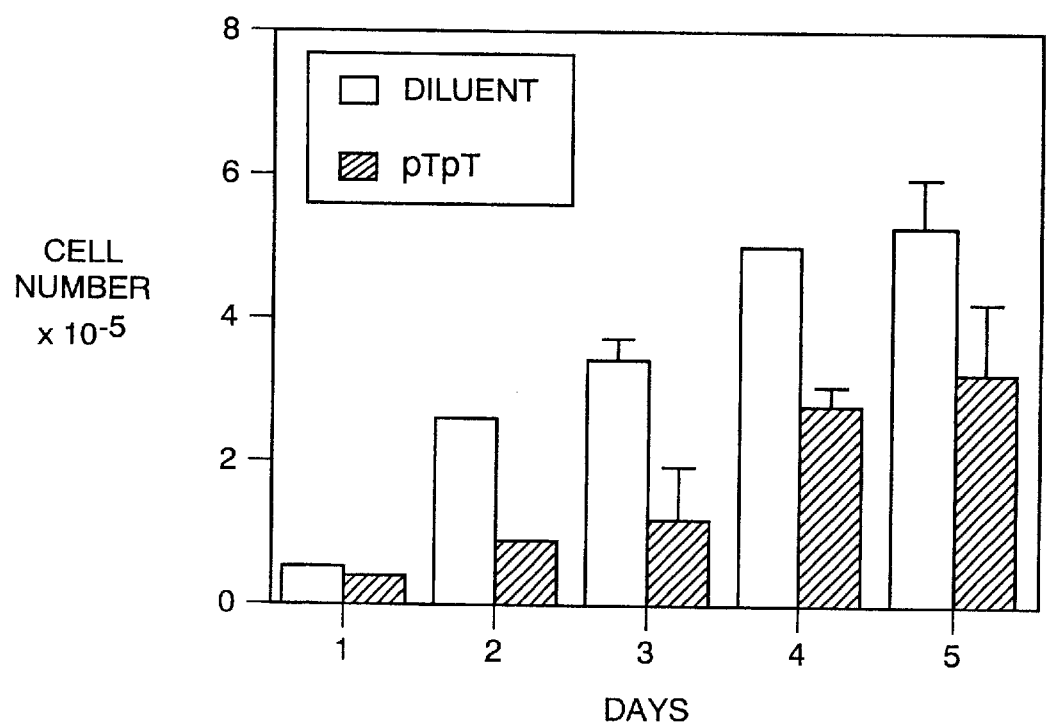
FIG. 8 is a graphic representation of the cell growth rate of normal human fibroblasts dosed with water (diluent) or 100 μM pTpT (T₂). Day 0 is before dosage. Values represent averages±standard deviations of duplicate cultures.

In a second experiment, normal human neonatal fibroblasts were plated and cultured, as described above in Example 1 for SCC12F cells. Cultures were supplemented with either 100 $\mu$l 2 $\mu$M $T_2$ or water (control), and cells were harvested for cell counts. The cell yield in fibroblast cultures treated with $T_2$ was reduced by 40% compared to that of paired control cultures after three days (FIG. 8). This corresponds to 4 population doublings in this time for control cells, compared with 3.6 doublings for $T_2$-treated cells. These results further demonstrate that application of the DNA fragments inhibits cell multiplication.

EXAMPLE 6

Effect of pTpT Applications on Epidermal Labeling Index

Guinea pigs received one or two daily topical applications of 100 $\mu$M pTpT, or vehicle alone as control, for three days. On the fourth day, punch biopsies were obtained and maintained for 7 or 8 hours in primary keratinocyte medium supplemented with 10 uCi/ml $^3$H-thymidine (specific activity 9.0 Ci/m mole, NEN). Tissues were then rinsed with cold medium and fixed in 10% phosphate buffered formalin. After a series of dehydration steps, tissues were embedded in paraffin. 6 um sections were cut and mounted onto glass slides, dipped in NTB-2 Nuclear Track emulsion and kept in the dark at 4° C. for 7 days. Sections were developed in Kodak D-19 developer and stained with hematoxylin and eosin. Labeling index was measured by calculating the percentage of labeled nuclei among 100 basal keratinocytes.

Results

| | Labeling Index |
|---|---|
| | 2 daily applications |
| Vehicle control | pTpT |
| 4 ± 1.4 | 1.5 ± 0.7 |
| | 1 daily application |
| Vehicle control | pTpT |
| 4.5 ± 2.1 | 2 ± 0 |

Results±SD are shown.
Labeling index (a measure of epidermal turnover rate) is less in pTpT-treated skin than in vehicle-treated skin, (>0.03 paired T test) in both experiments. These results demonstrate that the DNA fragments reduce epidermal turnover rate.

EXAMPLE 7

Role of p53 in DNA Repair

Figure 9:
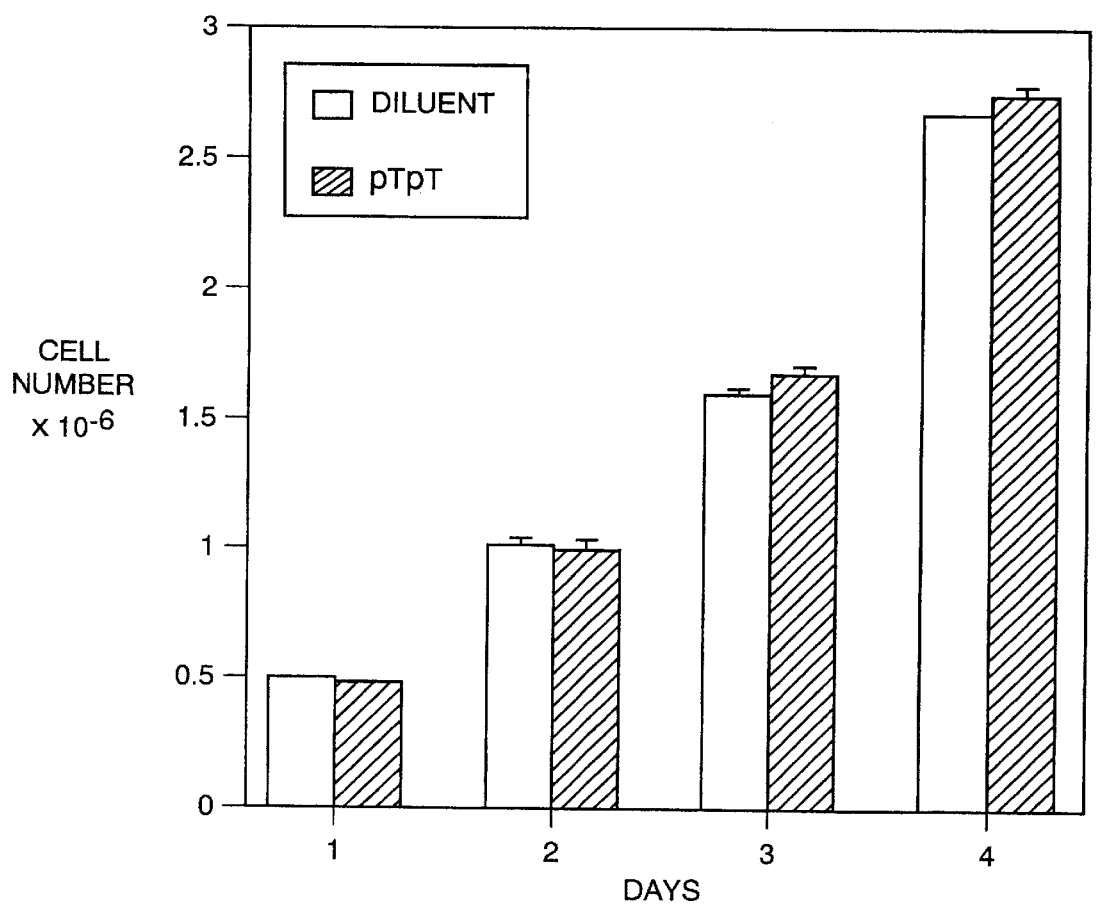
FIG. 9 is a graphic representation of the cell growth rate of p53-null H1299 lung carcinoma cells dosed with water (diluent) or 100 μM pTpT (T₂). Day 0 is before dosage; 1, 2, 3 and 4 are days after dosage. Values represent averages±standard deviations of duplicate cultures.

Both the GADD 45 and SDi 1 genes are known to be transcriptionally regulated by the tumor suppressor protein p53 (Kastan, M. B. et al., Cell 71:587–597 (1992); El-Deiry, W. S. et al., Cell 75:817–825 (1993)). After UV- and γ-irradiation, as well as treatment of cells with DNA-damaging chemical agents, there is a rapid stabilization and nuclear accumulation of p53 (Fritsche, M. et al., Oncogene 8:307–318 (1993); Nelson, W. G. and Kastan, M. B., Mol. Cell. Biol. 14:1815–1823 (1994); Lu, X. and Lane, D. P., Cell 75:765–778 (1993)), after which this protein binds to specific promoter consensus sequences and modulates the transcription of regulated genes (Lu, X. and Lane, D. P., Cell 75:765–778 (1993)). Recent data suggest that p53 can also be activated by the binding of small single-stranded DNAs, as well as certain peptides and antibodies, to a carboxyl terminal domain of this protein (Jayaraman, L. and Prives, C., Cell 81:1021–1029 (1995); Hupp, T. R. et al., Cell 83:237–245 (1995)). In order to determine whether the inhibitory effect of the dinucleotide pTpT on cell proliferation is mediated through p53, the growth response of a p53 null cell line, H1299 lung carcinoma cells, was examined. The p53-null H1299 cells (Sanchez, Y. et al., Science 271:357–360 (1996)) was maintained in DMEM with 10% calf serum. Preconfluent cultures were given fresh medium supplemented with either 100 $\mu$M pTpT or diluent. Cells were collected on consecutive days by trypsinization, and counted by Coulter counter. As shown in FIG. 9, there was no inhibition of proliferation of pTpT-treated H1299 cells compared to diluent-treated controls.

The effect of pTpT on the level and intracellular distribution of p53 in normal neonatal fibroblasts was examined by immunoperoxidase staining using a p53-specific monoclonal antibody (mAb 421, Oncogene, Cambridge, Mass.). Preconfluent cultures were treated with either 100 $\mu$M pTpT or diluent for 24 hours before cell staining. Cells were first fixed for one minute in Histochoice fixative (Amresco, Solon, Ohio) followed by a five-minute rinse in PBS. p53 was detected using the Vectastain Elite ABC kit (Vector Laboratories, Burlingame, Calif.) and the p53-specific monoclonal antibody nAb 421. Within 24 hours, an increase in intranuclear p53 was detected in pTpT-treated cells compared to diluent-treated cells (data not shown), as has been reported after UV-irradiation (Fritsche, M. et al., Oncogene 8:307–318 (1993); Nelson, W. G. and Kastan, M. B., Mol. Cell. Biol. 14:1815–1823 (1994); Lu, X. and Lane, D. P., Cell 75:765–778 (1993)). These results are consistent with the induction of the p53-regulated genes GADD 34 and SDI 1 in fibroblasts (data not shown) as well as in SCC12F cells, by pTpT.

In another experiment, pTpT was found to induce the expression of SDI 1 mRNA in a p53-dependent manner. Preconfluent cultures of H1299 cells were transfected with an expression vector containing the wild type human p53 cDNA under the control of the human cytomegalovirus promoter/enhancer (Dr. Bert Vogelstein, Johns Hopkins Oncology Center). Control transfections were performed using the vector from which the p53 cDNA was removed. Transfections were carried out using the Lipofectin Reagent Kit (GIBCO/BRL). One day after transfection, cells were collected for Western blot analysis using 20 $\mu$g total protein as described (Yaar, M. et al., J. Clin. Invest. 94:1550–1562 (1994)). p53 was detected using mAb 421, anti-mouse Ig linked to horseradish peroxidase (Amersham, Arlington Heights, Ill.) and an ECL-kit (Amersham) following the directions of the manufacturer. At the time of protein collection, duplicate cultures of H1299 cells transfected with the p53 expression vector (designated "p53") or control vector ("Ctrl") were given either diluent (DMEM) or 100 $\mu$M pTpT. After 24 hours, the cells were collected, processed for RNA isolation and Northern blot analysis with an SDI 1 cDNA probe. The autoradiograph was scanned using a Macintosh IIsi computer and Macintosh One Scanner, and the brightness and contrast were adjusted to display differences in autoradiographic signals maximally. The results indicated that p53-null H1299 cells express a very low level of the SDI 1 transcript and this level is not affected by addition of pTpT (data not shown). Transfection of these cells with a wild-type p53 expression vector increased the level of SDI 1 and rendered this transcript inducible by addition of pTpT (data not shown). Western analysis confirmed that H1299 cells normally express no p53 and that transfected H1299 cells expressed high levels of p53 (data not shown). These data strongly suggest that pTpT increases the transcriptional activity of p53.

EXAMPLE 8

Enhancement of DNA Repair

Expression of a UV-damaged reporter plasmid containing the bacterial chloramphenicolacetyltransferase (CAT) gene under the control of SV40 promoter and enhancer sequences, previously shown to detect decreased DNA repair capacity in human lymphocytes associated with aging and early-onset skin cancers (Wei, Q. et al., Proc. Natl. Acad. Sci.1 USA 90:1614–1618 (1993)), was used to measure the DNA repair capacity of normal neonatal human skin-derived fibroblasts and keratinocytes.

Newborn keratinocytes were established as described (Stanulis-Praeger, B. M. and Gilchrest, B. A., J. Cell. Physiol. 139:116–124 (1989)) using a modification of the method of Rheinwald and Green (Gilchrest, B. A. et al., J. Invest. Dermatol. 101:666–672 (1993)). First-passage keratinocytes were maintained in a non-differentiating low $Ca^{2+}$ medium (K-Stim, Collaborative Biomedical Products, Bedford, Mass.). Fibroblasts were established from dermal explants as described (Rheinwald, J. G. and Green, J., Cell 6:331–343 (1975)) and maintained in DMEM supplemented with 10% bovine serum. Cells were treated with either 100 $\mu$M pTpT or an equal volume of diluent (DMEM) for five days prior to transfection. Duplicate cultures of each condition were transfected using the Lipofectin Reagent Kit (GIBCO/BRL) and 5 $\mu$g reporter DNA, pCAT-control vector (Promega, Madison, Wis.). Before transfection, the vector DNA was either sham irradiated or exposed to 100 $mJ/cm^2$ UVB radiation from a 1 KW Xenon arc solar simulator (XMN 1000-21, Optical Radiation, Azuza, Calif.) metered at 285±5 nm using a research radiometer (model IL 1700A, International Light, Newburyport, Mass.), as described (Yaar, M. et al., J. Invest. Dermatol. 85:70–74 (1985)). Cells were collected 24 hours after transfection in a lysis buffer provided in the CAT Enzyme Assay System (Promega, Madison, Wis.) using a protocol provided by the manufacturer. CAT enzyme activity was determined using the liquid scintillation counting protocol and components of the assay system kit. Labeled chloramphenicol [50–60 mCl (1.85–2.22 GBq) mmol] was purchased from New England Nuclear (Boston, Mass.). Protein concentration in the cell extracts was determined by the method of Bradford (Anal. Biochem. 72:248 (1986)). CAT activity was expressed as c.p.m./100 $\mu$g protein and is represented as percent activity of cells transfected with sham-irradiated plasmid.

Figure 10:
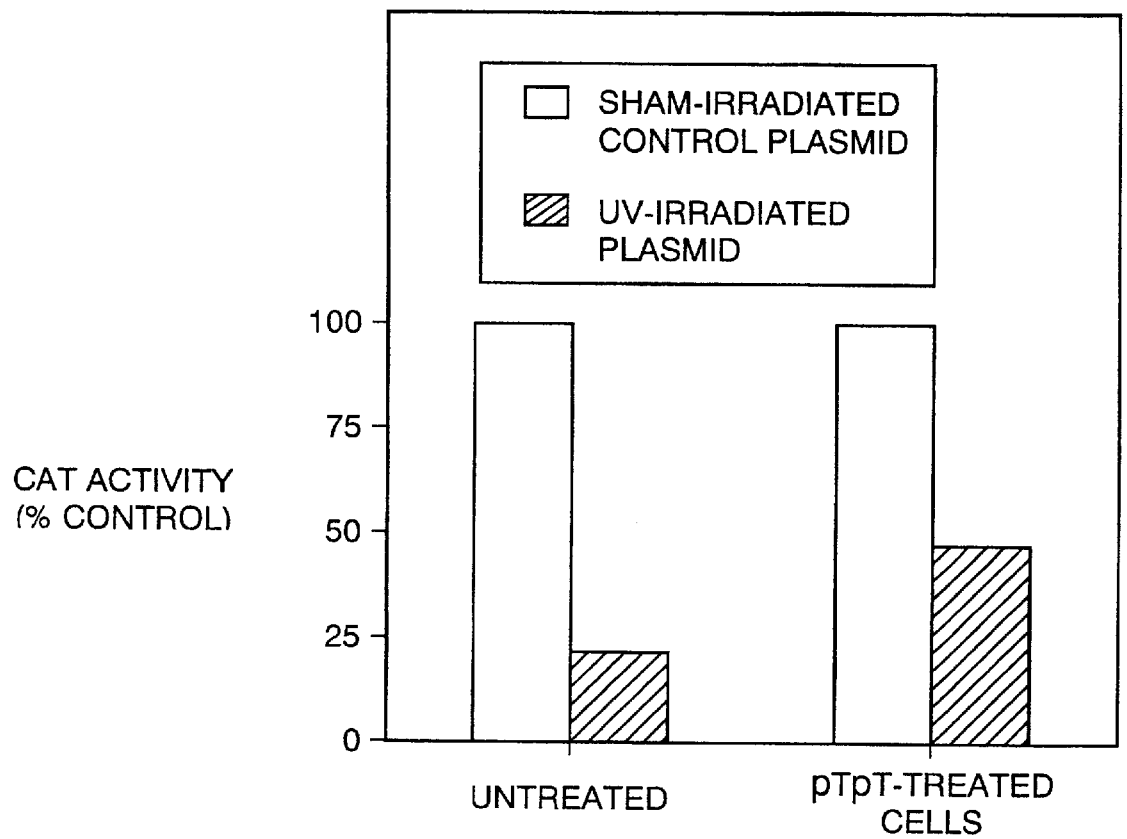
FIG. 10 is a graphic representation of enhancement of DNA repair of a reporter plasmid in human keratinocytes treated with pTpT. Open boxes, sham-irradiated control plasmid; filled boxes, UV-irradiated plasmid.
Figure 11:
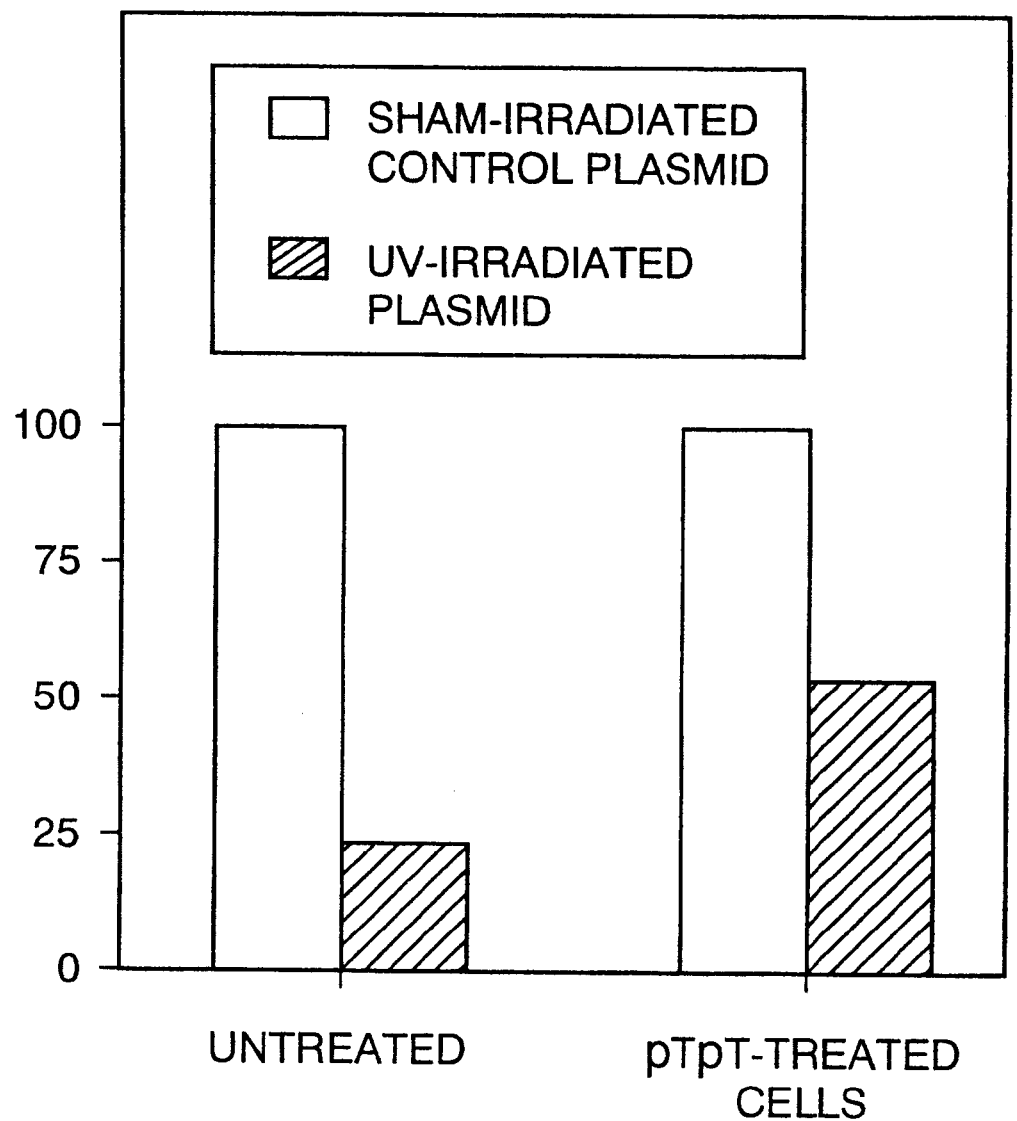
FIG. 11 is a graphic representation of enhancement of DNA repair of a reporter plasmid in human fibroblasts treated with pTpT. Open boxes, sham-irradiated control plasmid; filled boxes, UV-irradiated plasmid.

In preliminary experiments, exposure of the plasmid to a dose of solar-simulated irradiation (100 $mJ/cm^2$, metered at 285 nm) prior to transfection was identified as resulting in approximately 75% reduction in CAT activity assayed in cell lysates 16–24 hours after transfection, compared to that of sham-irradiated plasmid transfected into paired cultures. However, keratinocytes (FIG. 10) and fibroblasts (FIG. 11) pretreated with 100 $\mu$M pTpT for five days before transfection displayed CAT activity more than 50% that of sham-irradiated transfected controls. Because the reporter plasmid was nonreplicating, the level of CAT activity directly reflects the degree of DNA repair of the UV-damaged CAT gene restoring its biological activity. These data thus indicate that pTpT treatment of normal human fibroblasts and keratinocytes more than doubles the capacity of cells to repair UV-induced DNA damage over a 24 hour period. Cultured human cells have been shown to repair greater than 70% of UV-induced photoproducts within 24 hours after irradiation ((Mitchell, D. L. et al., Environmental UV Photobiology (Young, A. R. et al., eds), 345–377 (Plenum Press, New York and London, 1993)). The enhanced expression of Uv-irradiated plasmid in pTpT-treated cells did not result from a general increase in plasmid transcription in these cells, because the expression of the sham-irradiated plasmid was not higher than in non-pTpT-treated cells.

EXAMPLE 9

Activation of p53 and Repair of BP DNA Adducts

Cell Culture

Newborn human keratinocytes were established using a modification (Stanislus et al. *J. Invest. Dermatol.* 90:749–754 (1998)) of the method of Rheinwald and Green (*Cell* 6:331–343 (1975)). First-passage keratinocytes were maintained in a non-differentiating medium containing a low concentration of calcium ion (K-Stim, Collaborative Biomedical Products, Bedford, Mass.).

The p53-null H1299 lung carcinoma cell line (American Type Culture Collection, ATCC, Rockville, Md.) was maintained in Dulbeccols modified Eagle's medium (DMEM;GIBCO/BRL, Gaithersburg, Md.) supplemented with 10% bovine serum (Hyclone Labs, Logan, Utah).

Transfection of H1299 Cells With a p53 Expression Vector

Preconfluent cultures of H1299 cells were transfected with an expression vector containing the wild type human p53 cDNA under the control of the human cytomegalovirus promoter/enhancer (Dr. Bert Vogelstein, Johns Hopkins Oncology Center). Control transfections were performed using the same vector lacking the p53 cDNA. Transfections were carried out as described previously. One day after transfection, cells were collected for western blot using 20 $\mu$g total protein as described. p53 was detected using the monoclonal antibody Do-1 (Ab-6) known to detect both active and inactive forms of the protein (Oncogene, Cambridge, Mass.), anti-mouse Ig linked to horseradish peroxidase (Amersham, Arlington Heights, Ill.) and an ECL-kit (Amersham) following the direction of the manufacturer.

p53 Assay Using hGH Reporter Plasmid

Normal human keratinocytes were transfected with the human growth hormone (hGH) reporter plasmid (pPG-GH) using the Lipofectamine Reagent Kit (GIBCO/BRL) as suggested by the manufacturer and 0.5 $\mu$g pPG-GH added to each p35 culture dish. pPG-GH contains the hGH coding region under the control of the thymidine kinase (TK) promoter and p53 consensus sequence, and hGH protein production is known to be proportional to p53 activity (Kern et al., 1992). Transfection was performed in the presence of 100 $\mu$M pTpT (Midland Certified Reagent Company, Midland, Tex.) or an equal volume of diluent. At the same time the PS-$\beta$-galactosidase control vector (Promega, Madison, Wis.) was co transfected to determine the transfection efficiency (Norton and Coffin, 1985). Four hours after transfection, medium was removed and replaced with K-Stim medium with or without 100 $\mu$M pTpT. Twenty-four hours afer transfection and pTpT treatment, 400 $\mu$l of the medium was harvested from each 35 mm culture dish, and 100 $\mu$l of $^{125}$I-hGH antibody solution (Nichols Institute Diagnostics, San Juan Capistrano, Calif.) was added to detect secreted hGH. The cells were harvested in a Reporter Lysis Buffer (Promega) using a protocol provided by the manufacturer, and 150 $\mu$l of this lysate was used for the $\beta$-galactosidase assay using a $\beta$-galactosidase assay kit (Promega). Samples from each of triplicate culture dishes were evaluated for hGH and $\beta$-galactosidase synthesis.

H1299 cells were similarly transfected with p53 expression vector or control vector. Two days after the transfection these cells were cotransfected with pPG-GH and PSV-$\beta$-galactosidase control vector, and treated with 100 $\mu$M pTpT. Twenty four hours later, 250 $\mu$l of the medium and the cell lysate were harvested and processed as described above.

CAT Assay

The pCAT vector (Promega) was treated with benzo(a) pyrene-7,8-diol-9,10-epoxide (BPDE)- as described (Athas et al. *Cancer Res* 1991) to produce less damaged and more damaged plasmids, previously shown to be instructive in studies examining different repair capacities in human cells. Based on the incorporation of $^3$H-BPDE into the DNA, the less damaged plasmid contained 25 adducts per 5 kb plasmid and the more damaged plasmid contained 50 adducts. This non-replicating vector contains the chloramphenicol acetyltransferase gene under control of SV40 promoter and enhancer sequences. Human keratinocytes and p53-transfected H1299 cells were pre-treated with either 100 $\mu$M pTpT or an equal volume of diluent (DMEM) alone for 48 hours, then transfected with either BP-modified PCAT-control vector (0.5 $\mu$g/ml) or unmodified vector (0.5 $\mu$g/ml) together with PSV-p-galactosidase control vector (0.5 $\mu$g/ml). Cells were collected in a reporter lysis buffer (Promega) 24 hours after transfection. CAT enzyme activity was determined using the liquid scintillation counting protocol and components of the assay system kit (Promega). $^{14}$C-labeled chloramphenicol[50–60 mCi(1.85–2.22 GBq) mmol] was purchased from New England Nuclear (Boston, Mass.). CAT activity was normalized with $\beta$-galactosidase activity.

Western Blot Analysis

Cells were treated with 100 $\mu$M pTpT or an equal volume of diluent alone for 48 hours. Total cellular proteins were collected in a buffer consisting of 0.25 M Tris HCl (pH 7.5), 0.375 M NaCl, 2.5% sodium deoxycholate, 1% Triton X-100, 25 mM MgCl2, 1 mM phenylmethyl sulfonyl flouride, and 0.1 mgml aprotinin. Proteins (100 $\mu$g per sample) were separated by 7.5–15% SDS-PAGE and transferred to a nitrocellulose membrane (Schleicher & Schuell, Keene, N.H.). After transfer, the gel was stained with Coomassie Blue to verify even loading as visualized by the residual high molecular weight proteins. Membranes were blocked in 0.05% Tween-20/PBS with 5% milk, (Bio-Rad Laboratories, Hercules, Calif.). Antibody reactions were performed with the following antibodies: anti p53 (AB-6), anti PCNA (Ab-2) (Oncogene Science), and anti XPA (FL-273) (Santa Cruz Biotechnology). Sheep anti-mouse Ig linked to horseradish peroxidase (Amersham, Arlington Heights, Ill.) (for p53 and PCNA) and goat anti-rabbit IgG (Bio-Rad)(for XPA) were used as the secondary antibodies. Binding was detected by the ECL detection kit (Amersham).

To measure the repair of BP DNA adducts, non-replicating BP-damaged reporter plasmid system containing the bacterial chloramphenicol acetyltransferase (CAT) gene was used as described in Example 8. With first passage human keratinocytes, the transfection efficiency, as measured by the cotransfected $\beta$-galactosidase expression vector, was 40–70%. Compared to diluent-treated cells, pTpT-treated human keratinocytes showed an approximate doubling of CAT expression relative to paired cultures transfected with undamaged control CAT vector, when transfected with either the less BP-damaged (~25 adducts/ plasmid) or the more BP-damaged (~50 adducts/plasmid) vector.

To confirm the activation of p53 by pTpT in a second assay, a reporter plasmid expressing the human growth hormone (hGH) gene under the influence of a p53 inducible promoter was employed. Activation of p53 increases its binding to the consensus sequence in the plasmid, leading to transcription of the hGH coding sequence and ultimately to secretion of hGH into the medium.

pTpT-treated human keratinocytes showed a 45%±25% increase in hGH secretion compared to diluent-treated cells. These data indicate that pTpT activates p53 in normal human keratinocytes as well as in p53-transfected H1299 cells.

To confirm that pTpT enhances repair of BP-DNA adducts through p53 activation, p53-null H1299 cells were transfected with the p53 expression vector, and p53 protein expression was then confirmed by western blot analysis 48 hours after transfection. In parallel cultures, 48 hours after transfection with the p53 expression or control vector, then processed as described above. In p53+H1299 cells, repair was comparable to that observed in normal keratinocytes; and the plasmid containing a low level of BP damage was repaired 80%+50% more efficiently in pTpT-pre-treated cells than in diluent pre-treated cells; and the plasmid containing a high level of BP damage was repaired more than three times as efficiently. In p53-H1299 cells, however, the repair capacity was the same as in both treatment groups. These data demonstrate that enhanced repair of BP-DNA adducts by pTpT requires p53.

pTpT activation of p53 in H1299 cells transiently transfected with the p53-responsive-hGH+H1299 resulted in a 40% increase in hGH secretion compared to diluent-treated cells. These data further demonstrate that pTpT enhances p53 transcriptional activity through enhanced binding to its DNA consensus sequence.

Western blot analysis was used to examine the effect of pTpT treatment on the expression of selected genes known to be involved in DNA repair. Normal human keratinocytes were treated with pTpT for 2 days before harvesting cellular protein. pTpT up-regulated the levels of p53, PCNA and the XPA protein 2 to 3-fold within 2 days of treatment.

EXAMPLE 10

Inhibition of Contact Hypersensitivity in a Hurine Model

C57B16 mice were subjected to the following treatment prior to sensitization with the allergen DNFB, through abdominal skin; no pretreatment, UVB irradiation (200 $J/m^2/dx4$ d), pTpT, pApA, or vehicle alone (30 μl of 100 μM BID×5 d). Mice pretreated with UVB or pTpT showed markedly suppressed ear swelling responses to DNFB challenge (0.6±0.2 and 0.9±0.3) compared to untreated or vehicle treated animals (4.3±0.6 and 3.3±0.2), whereas pApA-treated mice exhibited intermediate responses (2.5±0.6). TNFA gene activation was measured by utilizing mice carrying a CAT reporter transgene bearing the entire TNFA promoter and 3'-untranslated region. Transgenic mice were subjected to the following treatment prior to skin assay for CAT expression: UVB irradiation (200–700 $J/m^2$), intracutaneous injection of pTpT (100 μM); lipopolysaccharide (LPS 1 μg/ml) as positive control, or vehicle alone. CAT activity was detected in skin treated with UVB, LPS, or pTpT (but not with vehicle alone).

EXAMPLE 11

Oligonucleotide Dependent UV-Mimetic Activity

The induction of melanogenesis in Cloudman S91 mouse melanoma cells by a five-nucleotide oligomer, CATAC, and a nine-nucleotide oligomer, GAGTATGAG (SEQ ID NO.1) was examined. Duplicates of Cloudman S91 murine melanoma cells were incubated with either 100 μM oligo or an equal volume of diluent ($H_2O$) for 5 days. The cells were then collected, counted, and pelleted for melanin analysis. In three experiments, the pigment content after incubation with the 9-mer, 5-mer and pTpT increased 418%±267%, 61%±60% and 155%±60% of control levels, respectively. The 9-mer, but not the 5-mer, also stimulated melanogenesis in human melanocytes, producing a 51–62% increase after one week in culture. As with pTpT, the 9-mer oligonucleotide, but not the 5-mer, also induced the expression of the p21/Waf 1/Cip 1 gene within 48 hours in a squamous cell carcinoma line, increasing the level of this mRNA 200–300%, compared to a 100–150% increase from pTpT. Variations of this oligonucleotide were evaluated: a scrambled 9-mer (TAGGAGGAT SEQ ID NO.2) and two truncated versions, a 7-mer (AGTATGA SEQ ID NO.3) and 5-mer (GTATG SEQ ID NO.4). Both 9-mers were equally active, inducing a 800% increase in melanin content. The truncated versions (7-mer and 5-mer) were also active, inducing 640% and 670% increases, respectively. Together, these data show that the UV-mimetic activity of pTpT can be duplicated quite dramatically by other oligonucleotides.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of treating psoriasis in a mammal, comprising administering topically to the epidermis of the mammal an effective amount of DNA fragments selected from the group consisting of: SEQ ID NO: 1, SEQ ID NO: 2 SEQ ID NO: 3 and SEQ ID NO: 4 and combinations thereof.

2. A method of treating vitiligo in a mammal, comprising administering topically to the epidermis of the mammal an effective amount of DNA fragments selected from the group consisting of: SEQ ID NO: 1 SEQ ID NO: 2 SEQ ID NO: 3 and SEQ ID NO: 4 and combinations thereof.

3. A method of reducing photoaging in a mammal, comprising administering topically to the epidermis of the mammal an effective amount of DNA fragments selected from the group consisting of: SEQ ID NO: 1 SEQ ID NO: 2 SEQ ID NO: 3 and SEQ ID NO: 4 and combinations thereof.

4. A method of reducing the likelihood of the development of skin cancer in a mammal, comprising administering topically to the epidermis of the mammal an effective amount of DNA fragments selected from the group consisting of: SEQ ID NO: 1, SEQ ID NO: 2 SEQ ID NO: 3 and SEQ ID NO: 4 and combinations thereof.

5. A method of treating hyperproliferative disease affecting skin cells in a mammal, comprising administering to the skin cells of interest in the mammal an effective amount of DNA fragments selected from the group consisting of: SEQ ID NO: 1, SEQ ID NO: 2, SEQ ID NO: 3 and SEQ ID NO: 4 and combinations thereof.

* * * * *